US00PP16730P2

(12) United States Plant Patent
Uchneat

(10) Patent No.: US PP16,730 P2
(45) Date of Patent: Jun. 27, 2006

(54) **DOUBLE *IMPATIENS* PLANT NAMED 'BALFIEROSE'**

(50) Latin Name: *Impatiens walleriana*
Varietal Denomination: Balfierose

(75) Inventor: Michael S. Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 79 days.

(21) Appl. No.: 11/017,578

(22) Filed: Dec. 20, 2004

(51) Int. Cl.
*A01H 5/00* (2006.01)

(52) U.S. Cl. ..... Plt./317
(58) Field of Classification Search ..... Plt./317
See application file for complete search history.

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct Double *Impatiens* plant named 'Balfierose' characterized by its fully double rose-colored flowers, dark green-colored foliage, compact, upright and mounded growth habit, and good basal branching character.

1 Drawing Sheet

Latin name of genus and species of plant claimed: *Impatiens walleriana.*
Variety denomination: 'Balfierose'.

BACKGROUND OF THE INVENTION

The present invention relates to a new and distinct cultivar of Double *Impatiens* plant botanically known as *Impatiens walleriana* and hereinafter referred to by the cultivar name 'Balfierose'.

The new cultivar originated in a controlled breeding program during May 2001 at Elburn, Ill. The objective of the breeding program was the development of new *Impatiens* cultivars with numerous fully double flowers, excellent basal branching, and upright compact growth habit.

The female (seed) parent of the new cultivar was the proprietary *Impatiens walleriana* selection designated 3389-1-1, not patented, characterized by its semi-double purple-colored flowers. The male (pollen) parent of the new cultivar was the proprietary *Impatiens walleriana* selection designated 3457-1, not patented, characterized by its red-colored flowers. The new cultivar was discovered and selected by the inventor as a single flowering plant within the progeny of the stated cross-pollination during February 2002 at Elburn Ill.

Asexual reproduction of the new cultivar by terminal stem cuttings since February 2002 at West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfierose' as a new and distinct cultivar of Double *Impatiens* plant:

1. Fully double rose-colored flowers.
2. Dark green-colored foliage.
3. Good basal branching character.
4. Compact, upright and mounded growth habit.

Plants of the new cultivar differ from plants of the female parent primarily in flower form and color and from the male parent primarily in flower color.

Of the many commercially available Double *Impatiens* cultivars known to the inventor, the most similar to the new cultivar is the *Impatiens* walleriana variety 'Balolerose', U.S. Plant Pat. No. 15,164. However, in a side-by-side comparison conducted at West Chicago, Ill., plants of the new cultivar differed from plants of 'Balolerose' in the following characteristics:

1. The flowers of the new cultivar are larger than the flowers of 'Balolerose'.
2. The plants of the new cultivar are taller and wider than the plants of 'Balolerose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balfierose'. The plants were grown for 7 weeks in a greenhouse at West Chicago, Ill.

DETAILED BOTANICAL DESCRIPTION

Figure 1:
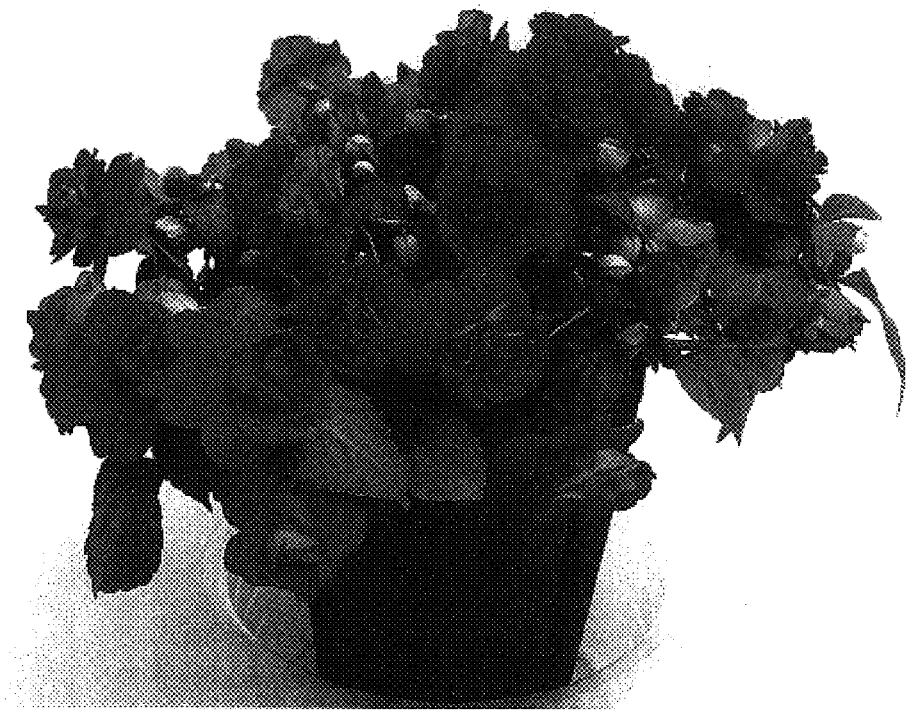
FIG. 1 illustrates a side view of the overall growth and flowering habit of 'Balfierose'.
Figure 2:
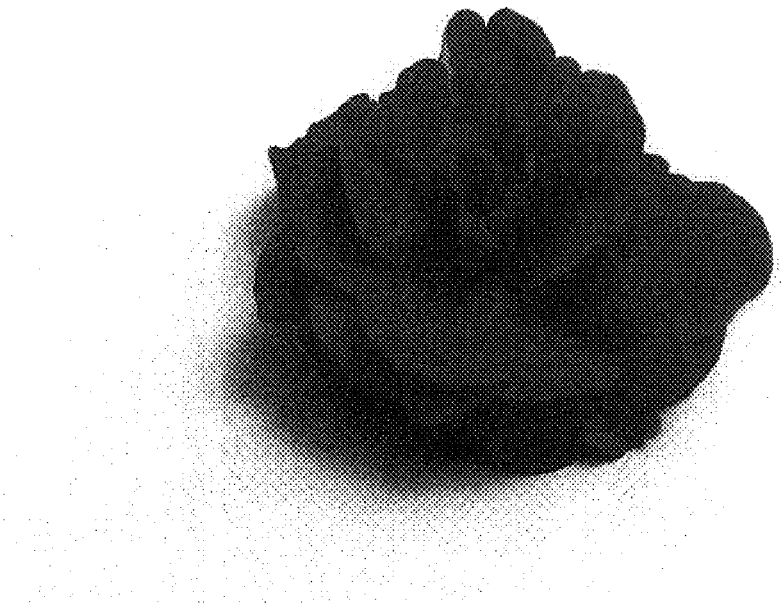
FIG. 2 illustrates a close-up view of an individual flower of 'Balfierose'.

The new cultivar has not been observed under all possible environmental conditions to date. Accordingly, it is possible that the phenotype may vary somewhat with variations in the environment, such as temperature, light intensity, and day length without, however, any variance in phenotype.

The chart used in the identification of colors described herein is The R.H.S. Colour Chart of The Royal Horticultural Society, London, England, 2001 edition, except where general color terms of ordinary significance are used. The color values were determined on Jul. 20, 2004 between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 7 weeks using a soil-less growth medium. Greenhouse temperatures were maintained at approximately 65°–75° F. during the day and approximately 55°–62° F. during the night. Greenhouse light levels were maintained at approximately 4,000–6,000 footcandles during the day.

Botanical classification: *Impatiens walleriana* cultivar Balfierose.

Parentage:

*Female (seed) parent.*—Proprietary *Impatiens walleriana* selection designated 3389-1-1, not patented.

*Male (pollen) parent.*—Proprietary *Impatiens walleriana* selection designated 3457-1, not patented.

Propagation:

*Type cutting.*—Terminal stem.

*Time to initiate roots.*—Approximately 5–8 days.

*Time to produce a rooted cutting.*—Approximately 14–21 days.

*Root description.*—Fine, fibrous.

*Rooting habit.*—Freely branching.

Plant description:

*Crop time.*—Approximately 6–8 weeks.

*Growth habit.*—Compact with good basal branching.

*Form.*—Upright and mounded.

*Size.*—Height from top of soil to top of plant plane: Approximately 15.6 cm. Width (area of plant spread): Approximately 27.4 cm.

*Branch.*—Quantity: Approximately 4 per plant. Strength: Strong. Length: Approximately 11.8 cm. Diameter: Approximately 1.0 cm. Texture: Glabrous. Color: 146B with streaks and around nodes of 187A. Internode length: Approximately 2.2 cm.

*Foliage.*—Quantity per branch: Approximately 20. Fragrance: None. Type: Simple. Arrangement: Alternate. Aspect: At right angle to stem. Shape: Ovate. Apex: Acuminate. Base: Cuneate. Margin: Crenate/ciliate. Venation pattern: Pinnate, arcuate. Length of mature foliage: Approximately 6.4 cm. Width of mature foliage: Approximately 3.4 cm. Texture of both surfaces of mature foliage: Glabrous. Color of upper surface of mature foliage: Darker than 147A, with veins and mid-vein of 146B. Color of lower surface of mature foliage: Closest to 148C with splotches of 183C and veins and mid-vein of 146B. Petiole length: Approximately 1.4 cm. Petiole diameter: Approximately 1.9 mm. Petiole texture: Both surfaces are glabrous. Petiole color: 148C with streaks of 183C.

Flowering description:

*Flowering habit.*—Freely flowering under outdoor growing conditions with substantially continuous blooming from spring through autumn and year round in greenhouse environment.

*Lastingness of individual bloom.*—Approximately 7–10 days.

*Quantity of flowers and buds.*—Approximately 18 fully open flowers and 20 buds showing color per plant at any one time.

Flower description:

*Flower bud rate of opening.*—Generally it takes from 2–4 days for buds to progress from first color to fully open flowers.

*Mature flower buds (just before opening).*—Shape: Elliptic. Length: Approximately 1.1 cm. Diameter: Approximately 8.1 mm. Color: 75B.

*Flower description.*—Type: Fully double. Fragrance: None. Shape: Spherical. Diameter: Approximately 3.6 cm. Depth: Approximately 2.8 cm. Borne: Above foliage facing upward or outward. Flowers are not persistent or fragrant.

*Petals.*—Quantity per flower: Approximately 28. Shape: Obovate. Margin: Entire. Apex: Obtuse. Base: Attenuate. Texture: Glabrous. Appearance: Iridescent. Size of outermost petals: Length: Approximately 2.1 cm. Width: 1.6 cm. Size of innermost petals: Length: 1.6 cm. Width: 1.3 cm.

*Flower color.*—Upper surface of petals when fully open: Closest to but not quite as blue as 58A. Lower surface of petals when fully open: Lighter than 73B.

*Calyx.*—Quantity of sepals: Three, with the lower sepal modified into a spur. Sepal apex: Acuminate. Sepal texture: Both surfaces are glabrous. Lateral sepal shape: Lanceolate. Lateral sepal apex: Acute. Lateral sepal length: Approximately 1.9 mm. Lateral sepal width: Approximately 0.6 mm. Lateral sepal color: Both surfaces are 144A. Lower sepal shape: Ovate. Lower sepal apex: Cuspidate. Lower sepal base forms spur. Lower sepal length: Approximately 1.2 cm. Lower sepal width: Approximately 8.5 mm. Lower sepal color: 145C at base, 145A at tip.

*Spur.*—Quantity: One per flower. Length: Approximately 2.6 cm. Diameter at base: Approximately 1.2 mm. Diameter at tip: Approximately 0.4 mm. Texture: Glabrous. Color: 145A with overlay of 187D and tip of 187A.

*Peduncles.*—Length: Approximately 1.2 cm. Diameter: Approximately 1.2 mm. Texture: Glabrous. Strength: Strong. Angle to stem: Acute. Color: 145B with overlay of 187D.

*Reproductive organs.*—None observed.

Seed and fruit development: Neither seed nor fruit production has been observed.

Disease and pest resistance: Resistance to pathogens and pests common to *Impatiens* has not been observed.

What is claimed is:

1. A new and distinct cultivar of Double *Impatiens* plant named 'Balfierose', substantially as herein shown and described.

* * * * *